US008962833B2

(12) United States Patent
Reddy et al.

(10) Patent No.: US 8,962,833 B2
(45) Date of Patent: Feb. 24, 2015

(54) SALTS OF RALTEGRAVIR

(75) Inventors: Bandi Parthasaradhi Reddy, Andhra Pradesh (IN); Kura Rathnakar Reddy, Andhra Pradesh (IN); Dasari Muralidhara Reddy, Andhra Pradesh (IN); Rapolu Raji Reddy, Andhra Pradesh (IN); Kesireddy Subash Chander Reddy, Andhra Pradesh (IN); Bandi Vamsi Krishna, Andhra Pradesh (IN)

(73) Assignee: Hetero Research Foundation (IN)

( * ) Notice: Subject to any disclaimer, the term of this patent is extended or adjusted under 35 U.S.C. 154(b) by 0 days.

(21) Appl. No.: 13/699,368

(22) PCT Filed: May 25, 2010

(86) PCT No.: PCT/IN2010/000354
§ 371 (c)(1),
(2), (4) Date: Feb. 14, 2013

(87) PCT Pub. No.: WO2011/148381
PCT Pub. Date: Dec. 1, 2011

(65) Prior Publication Data
US 2013/0137868 A1     May 30, 2013

(51) Int. Cl.
*C07D 413/12* (2006.01)
*A61K 31/513* (2006.01)

(52) U.S. Cl.
CPC ............ *C07D 413/12* (2013.01); *A61K 31/513* (2013.01)
USPC ........................................................ 544/319

(58) Field of Classification Search
USPC .......................................................... 544/319
See application file for complete search history.

(56) References Cited

U.S. PATENT DOCUMENTS

2006/0122205 A1*   6/2006   Belyk et al. .................... 514/269
2009/0298869 A1   12/2009   Burnier et al.

FOREIGN PATENT DOCUMENTS

WO          03035077 A1     5/2003
WO     2006060712 A2     6/2006
WO     2010140156 A2   12/2010

OTHER PUBLICATIONS

International Search Report and Written Opinion; International Application No. PCT/IN2010/00354; International Filing Date May 25, 2010; Date of Mailing Feb. 8, 2011; Applicant's File Reference HET0075US; 8 pages.

* cited by examiner

*Primary Examiner* — Kristin Vajda
*Assistant Examiner* — Valerie Rodriguez-Garcia
(74) *Attorney, Agent, or Firm* — Cantor Colburn LLP (57) ABSTRACT

The present invention provides novel salts of raltegravir, processes for their preparation and pharmaceutical compositions comprising them. The present invention also provides crystalline sodium salt of raltegravir, process for its preparation and pharmaceutical compositions comprising it. The present invention further provides a process for the preparation of amorphous sodium salt of raltegravir. The present invention further provides a process for the preparation of raltegravir potassium crystalline form H1.

3 Claims, 11 Drawing Sheets

SALTS OF RALTEGRAVIR

CROSS-REFERENCE TO RELATED APPLICATIONS

This application is a 371 of PCT/IN2010/000354, filed on May 25, 2010, under the provisions of 35 U.S.C. 119 and the International Convention for the protection of Industrial Property, which are incorporated herein by reference.

FIELD OF THE INVENTION

The present invention provides novel salts of raltegravir, processes for their preparation and pharmaceutical compositions comprising them. The present invention also provides crystalline sodium salt of raltegravir, process for its preparation and pharmaceutical compositions comprising it. The present invention further provides a process for the preparation of amorphous sodium salt of raltegravir. The present invention further provides a process for the preparation of raltegravir potassium crystalline form H1.

BACKGROUND OF THE INVENTION

Inhibitors of human immunodeficiency virus (HIV) protease have been approved for use in the treatment of HIV infection for several years. A particularly effective HIV integrase inhibitor is N-(4-fluorobenzyl)-5-hydroxy-1-methyl-2-(1-methyl-1-{[(5-methyl-1,3,4-oxadiazol-2-yl)carbonyl]amino}ethyl)-6-oxo-1,6-dihydropyrimidine-4-carboxamide, also known as raltegravir and its pharmaceutically acceptable salts such as raltegravir potassium. Raltegravir is represented by the following structure.

Polymorphism is defined as "the ability of a substance to exist as two or more crystalline phases that have different arrangement and/or conformations of the molecules in the crystal Lattice. Thus, in the strict sense, polymorphs are different crystalline forms of the same pure substance in which the molecules have different arrangements and/or different configurations of the molecules". Different polymorphs may differ in their physical properties such as melting point, solubility, X-ray diffraction patterns, etc. Although those differences disappear once the compound is dissolved, they can appreciably influence pharmaceutically relevant properties of the solid form, such as handling properties, dissolution rate and stability. Such properties can significantly influence the processing, shelf life, and commercial acceptance of a polymorph. It is therefore important to investigate all solid forms of a drug, including all polymorphic forms, and to determine the stability, dissolution and flow properties of each polymorphic form. Polymorphic forms of a compound can be distinguished in the laboratory by analytical methods such as X-ray diffraction (XRD), Differential Scanning Calorimetry (DSC) and Infrared spectrometry (IR).

Solvent medium and mode of crystallization play very important role in obtaining a crystalline form over the other.

Raltegravir and its salts can exist in different polymorphic forms, which differ from each other in terms of stability, physical properties, spectral data and methods of preparation.

WO Patent Publication No. 03/035077 disclosed N-substituted 5-hydroxy-6-oxo-1,6-dihydropyrimidine-4-carboxamides and pharmaceutically acceptable salts thereof. Processes for the preparations of raltegravir and related compounds were disclosed in WO Patent No. 03/035077. According to WO Patent No. 03/035077, raltegravir is prepared by reacting 5-methyl-1,3,4-oxadiazole-2-carboxylic acid with 2-(1-amino-1-methylethyl)-N-(4-fluorobenzyl)-5-hydroxy-1-methyl-6-oxo-1,6-dihydropyrimidine-4-carboxamide in acetonitrile in presence of triethyl amine and N,N-dimethylformamide.

WO Patent Publication No. 2006/060712 disclosed potassium salt of raltegravir. The publication described the formation of two crystalline forms of raltegravir potassium, which were designated raltegravir potassium salt of crystalline anhydrous Form 1 and crystalline hydrated Form 2. The patent publication noted that attempts to prepare a crystalline sodium salt of raltegravir was unsuccessful, resulting only in amorphous material.

We have discovered that sodium of raltegravir can also be existed as a crystalline product.

Amorphous form and crystalline form H1 of raltegravir potassium were disclosed in co-pending application no. PCT/IN2009/000317.

We have discovered novel salts of raltegravir such as barium, calcium and lithium, and also discovered a process for the preparation of amorphous sodium salt of raltegravir and a process for the preparation of raltegravir potassium crystalline form H1.

Thus, one object of the present invention is to provide a barium salt of raltegravir, process for its preparation and pharmaceutical composition comprising it.

Another object of the present invention is to provide a calcium salt of raltegravir, process for its preparation and pharmaceutical composition comprising it.

Another object of the present invention is to provide a lithium salt of raltegravir, process for its preparation and pharmaceutical composition comprising it.

Another object of the present invention is to provide crystalline sodium salt of raltegravir, process for its preparation and pharmaceutical composition comprising it.

Another object of the present invention is to provide a process for the preparation of amorphous sodium salt of raltegravir.

The salt of the present invention may also serve as intermediate for preparation of raltegravir free base or another salt of raltegravir.

Yet another object of the present invention is to provide a process for the preparation of raltegravir potassium crystalline form H1.

SUMMARY OF THE INVENTION

In one aspect, the present invention provides a barium salt of raltegravir, that is, raltegravir barium.

In another aspect, the present invention provides a process for the preparation of raltegravir barium, which comprises:
a) reacting raltegravir with barium hydroxide in a suitable solvent;
b) heating the contents to an elevated temperature;
c) slurrying the solution obtained in step (b); and
d) isolating raltegravir barium.

In another aspect, the present invention provides a pharmaceutical composition comprising raltegravir barium and a pharmaceutically acceptable excipient.

In another aspect, the present invention provides a calcium salt of raltegravir, that is, raltegravir calcium.

In another aspect, the present invention provides a process for the preparation of raltegravir calcium, which comprises:
a) reacting raltegravir with calcium acetate in a suitable solvent;
b) heating the contents to an elevated temperature;
c) removing the solvent from the solution obtained in step (b) to obtain a residual mass;
d) slurrying the residual mass obtained in step (c) with aliphatic hydrocarbon solvent; and
e) isolating raltegravir calcium.

In another aspect, the present invention provides a pharmaceutical composition comprising raltegravir calcium and a pharmaceutically acceptable excipient.

In another aspect, the present invention provides a lithium salt of raltegravir, that is, raltegravir lithium.

In another aspect, the present invention provides a process for the preparation of raltegravir lithium, which comprises:
a) reacting raltegravir with lithium hydroxide in a suitable solvent;
b) heating the contents to an elevated temperature;
c) removing the solvent from the solution obtained in step (b) to obtain a residual mass;
d) slurrying the residual mass obtained in step (c) with alcoholic solvent; and
e) isolating raltegravir lithium.

In another aspect, the present invention provides a pharmaceutical composition comprising raltegravir lithium and a pharmaceutically acceptable excipient.

In another aspect, the present invention provides crystalline raltegravir sodium.

In another aspect, the present invention provides a process for the preparation of crystalline raltegravir sodium, which comprises:
a) suspending raltegravir in an alcoholic solvent;
b) adding sodium hydroxide to the suspension obtained in step (a);
c) slurrying the reaction mass obtained in step (b) at about 25 to 30° C.; and
d) isolating crystalline raltegravir sodium.

In another aspect, the present invention provides a process for the preparation of crystalline form 1 of raltegravir sodium, which comprises:
a) suspending raltegravir in an alcoholic solvent;
b) adding sodium hydroxide to the suspension obtained in step (a);
c) slurrying the reaction mass obtained in step (b) for 10 to 12 hours at about 25 to 30° C.; and
d) isolating raltegravir sodium crystalline form 1.

In another aspect, the present invention provides a process for the preparation of crystalline form 2 of raltegravir sodium, which comprises:
a) suspending raltegravir in an alcoholic solvent;
b) adding sodium hydroxide to the suspension obtained in step (a);
c) slurrying the reaction mass obtained in step (b) for 30 to 35 hours at about 25 to 30° C.; and
d) isolating raltegravir sodium crystalline form 2.

In another aspect, the present invention provides a pharmaceutical composition comprising crystalline raltegravir sodium and a pharmaceutically acceptable excipient.

In another aspect, the present invention provides a process for the preparation of amorphous raltegravir sodium, which comprises:
a) reacting raltegravir with sodium hydroxide in a suitable solvent;
b) heating the contents to an elevated temperature;
c) removing the solvent from the solution obtained in step (b) to obtain a residual mass;
d) slurrying the residual mass obtained in step (c) with aliphatic hydrocarbon solvent; and
e) isolating amorphous raltegravir sodium.

Yet another aspect, the present invention provides a process for the preparation of raltegravir potassium crystalline form H1, which comprises:
a) suspending raltegravir in an alcoholic solvent;
b) adding potassium hydroxide to the suspension obtained in step (a);
c) slurrying the reaction mass obtained in step (b); and
d) isolating raltegravir potassium crystalline form H1.

X-ray powder diffraction spectrum was measured on a bruker axs D8 advance X-ray powder diffractometer having a copper-Kα radiation. Approximately 1 gm of sample was gently flattered on a sample holder and scanned from 2 to 50 degrees two-theta, at 0.019 degrees to theta per step and a step of 119 seconds. The sample was simply placed on the sample holder. The sample was rotated at 30 rpm at a voltage 40 KV and current 35 mA.

DSC (Differential Scanning Calorimetry) measurements were performed with a DSC Q10 (TA Instruments, Inc.). About 2.3 mg of the powder was placed in an open aluminum pan and it was crimped with an aluminum lid. The crimped sample was then placed in the DSC cell opposite to empty aluminum pan (as reference) and the sample was scanned at 10 deg C./min from 50 deg C. to 300 deg C.

DETAILED DESCRIPTION OF THE INVENTION

According to one aspect of the present invention, there is provided a barium salt of raltegravir, that is, raltegravir barium.

The term "raltegravir barium" as used herein means any salt comprising raltegravir anions and barium cations.

The raltegravir barium may preferably be a solid.

Figure 1:
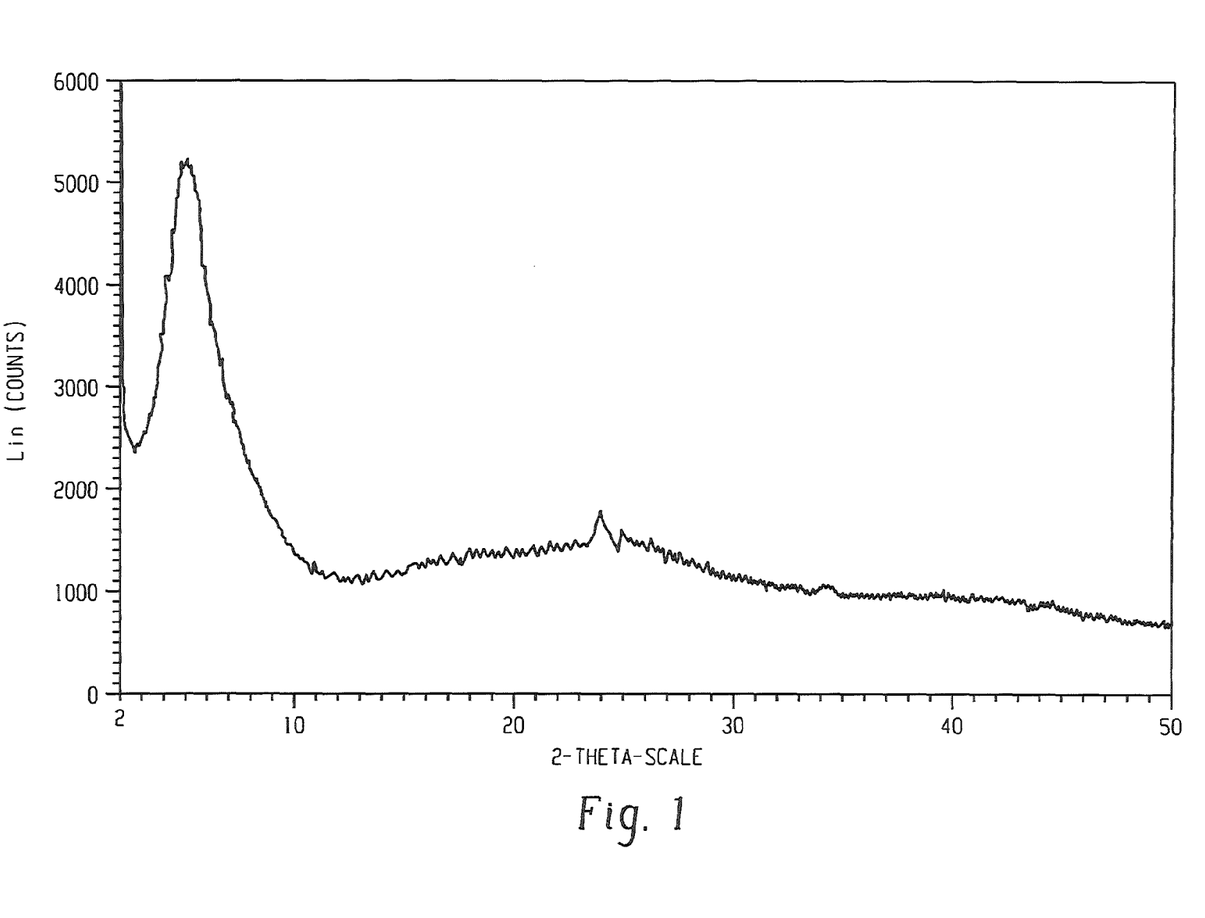
FIG. 1 is X-ray powder diffraction spectrum of amorphous raltegravir barium.

The powdered x-ray diffractogram (PXRD) of amorphous raltegravir barium is shown in FIG. 1.

Figure 2:
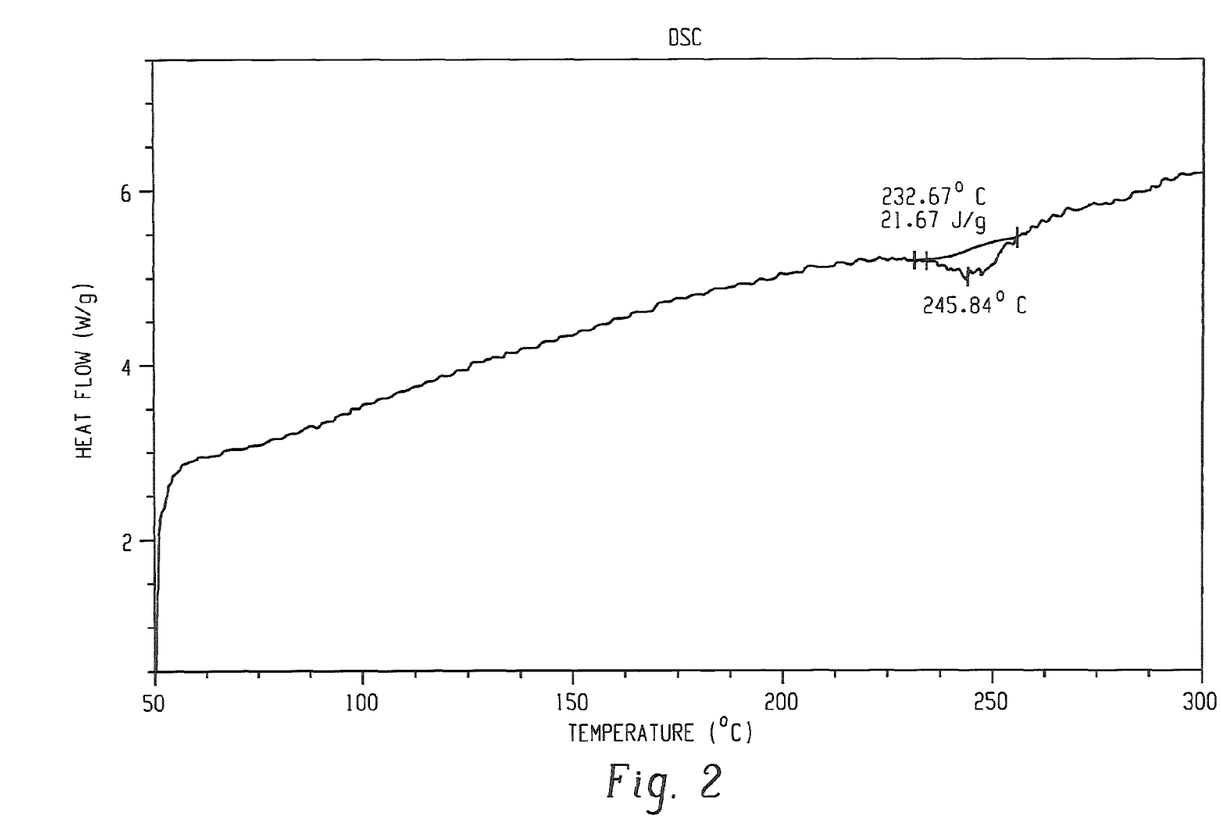
FIG. 2 is Differential scanning calorimetry (DSC) thermogram of amorphous raltegravir barium.

Amorphous raltegravir barium of present invention is further characterized by a differential scanning calorimetry (DSC) thermogram as shown in FIG. 2.

According to another aspect of the present invention, there is provided a process for the preparation of raltegravir barium, which comprises:
a) reacting raltegravir with barium hydroxide in a suitable solvent;
b) heating the contents to an elevated temperature;
c) slurrying the solution obtained in step (b); and
d) isolating raltegravir barium.

The suitable solvent used in the process may preferably be a solvent or mixture of solvents selected from the group consisting of water; an alcoholic solvents such as methanol, ethanol and isopropyl alcohol; an ester solvents such as ethyl acetate, methyl acetate, isopropyl acetate, tert-butyl methyl acetate and ethyl formate; a nitrile solvents such as acetonitrile, propionitrile, butyronitrile and benzonitrile; dimethylformamide; dimethylsulfoxide; an aromatic hydrocarbon solvents such as benzene, toluene and xylene; a halogenated hydrocarbon solvents such as methylene chloride, chloroform, carbontetrachloride and ethylene dichloride; a ketonic solvents such as acetone, methyl ethyl ketone, methyl isobutyl ketone and diethyl ketone; an ether solvents such as tetrahydrofuran, 1,4-dioxane, tert-butyl methyl ether and diethyl ether. More preferable solvent is water, alcoholic solvents and nitrile solvents, and still more preferable solvent is water, methanol, ethanol and acetonitrile.

The term "elevated temperature" refers to temperature at above 25° C. Preferably the contents are heating in step (b) at about 60 to 70° C.

Isolation of raltegravir barium in step (d) may preferably be performed by conventional techniques such as centrifugation and filtration.

According to another aspect of the present invention, there is provided a pharmaceutical composition that comprises raltegravir barium and pharmaceutically acceptable carriers, diluents or excipients and optionally other therapeutic ingredients.

The salt may preferable be conveniently formulated into tablets, capsules, suspensions, dispersions, injectables and other pharmaceutical forms.

According to another aspect of the present invention, there is provided a calcium salt of raltegravir, that is, raltegravir calcium.

The term "raltegravir calcium" as used herein means any salt comprising raltegravir anions and calcium cations.

The raltegravir calcium may preferably be a solid.

Figure 3:
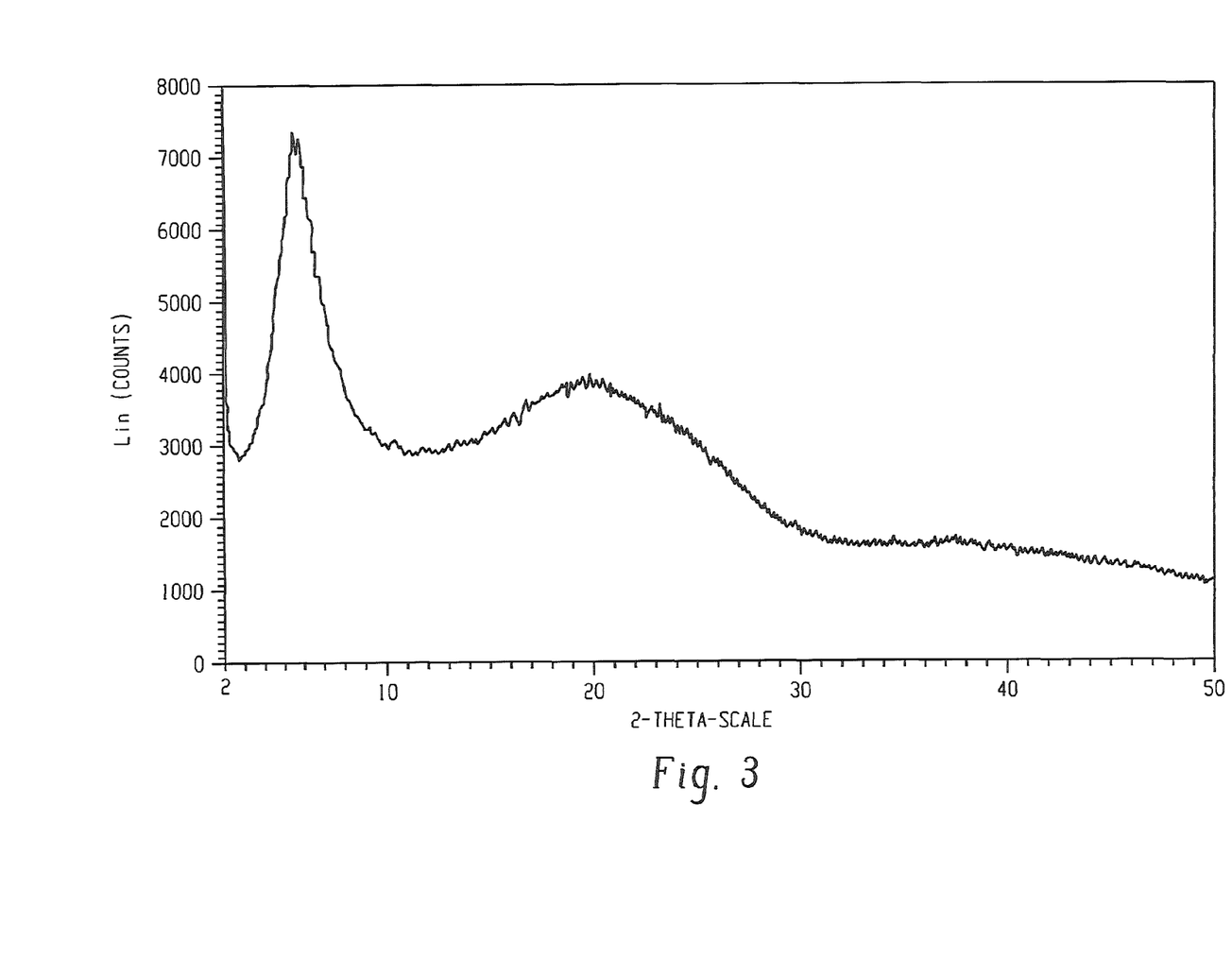
FIG. 3 is X-ray powder diffraction spectrum of amorphous raltegravir calcium.

The powdered x-ray diffractogram (PXRD) of amorphous raltegravir calcium is shown in FIG. 3.

Figure 4:
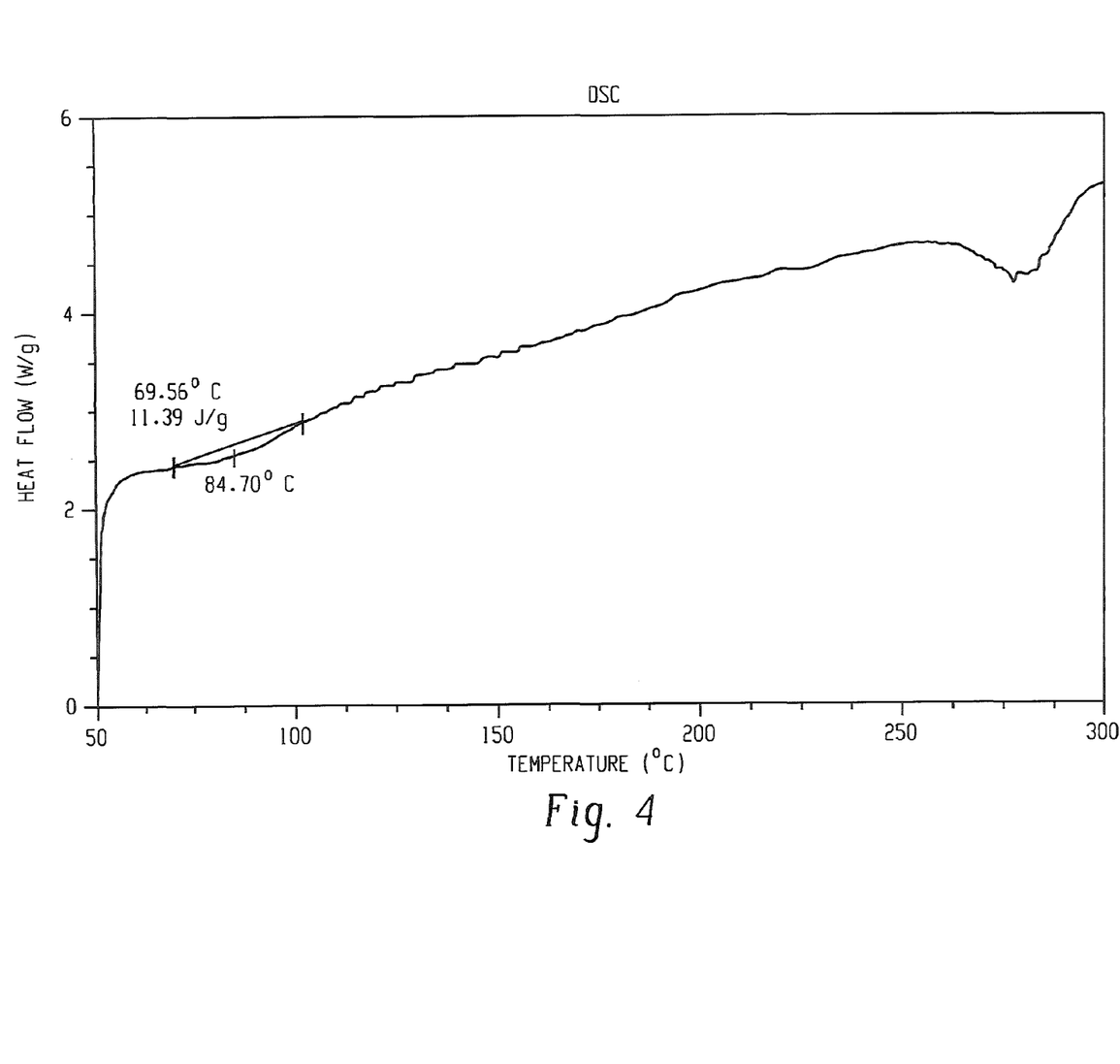
FIG. 4 is Differential scanning calorimetry (DSC) thermogram of amorphous raltegravir calcium.

Amorphous raltegravir calcium of present invention is further characterized by a differential scanning calorimetry (DSC) thermogram as shown in FIG. 4.

According to another aspect of the present invention, there is provided a process for the preparation of raltegravir calcium, which comprises:
a) reacting raltegravir with calcium acetate in a suitable solvent;
b) heating the contents to an elevated temperature;
c) removing the solvent from the solution obtained in step (b) to obtain a residual mass;
d) slurrying the residual mass obtained in step (c) with aliphatic hydrocarbon solvent; and
e) isolating raltegravir calcium.

The suitable solvent used in step (a) may preferably be a solvent or mixture of solvents selected from the group consisting of water; an alcoholic solvents such as methanol, ethanol and isopropyl alcohol; an ester solvents such as ethyl acetate, methyl acetate, isopropyl acetate, tert-butyl methyl acetate and ethyl formate; a nitrile solvents such as acetonitrile, propionitrile, butyronitrile and benzonitrile; dimethylformamide; dimethylsulfoxide; an aromatic hydrocarbon solvents such as benzene, toluene and xylene; a halogenated hydrocarbon solvents such as methylene chloride, chloroform, carbontetrachloride and ethylene dichloride; a ketonic solvents such as acetone, methyl ethyl ketone, methyl isobutyl ketone and diethyl ketone; an ether solvents such as tetrahydrofuran, 1,4-dioxane, tert-butyl methyl ether and diethyl ether. More preferable solvent is water, alcoholic solvents and nitrile solvents, and still more preferable solvent is water, methanol, ethanol and acetonitrile.

The term "elevated temperature" refers to temperature at above 25° C. Preferably the contents are heating in step (b) at about 60 to 70° C.

Removal of the solvent may be carried out in step (c) at atmospheric pressure or at reduced pressure. Removal of the solvent may preferably be carried out until the solvent is almost completely distilled off.

The aliphatic hydrocarbon solvent used in step (d) may preferably be a solvent or a mixture of solvents selected from cyclohexane, hexane and n-heptane. More preferable aliphatic hydrocarbon solvent is n-heptane.

Isolation of raltegravir calcium in step (e) may preferably be performed by conventional techniques such as centrifugation and filtration.

According to another aspect of the present invention, there is provided a pharmaceutical composition that comprises raltegravir calcium and pharmaceutically acceptable carriers, diluents or excipients and optionally other therapeutic ingredients. The salt may preferable be conveniently formulated into tablets, capsules, suspensions, dispersions, injectables and other pharmaceutical forms.

According to another aspect of the present invention, there is provided a lithium salt of raltegravir, that is, raltegravir lithium.

The term "raltegravir lithium" as used herein means any salt comprising raltegravir anions and lithium cations.

The raltegravir lithium may preferably be a solid and more preferable solid is crystalline raltegravir lithium.

Figure 5:
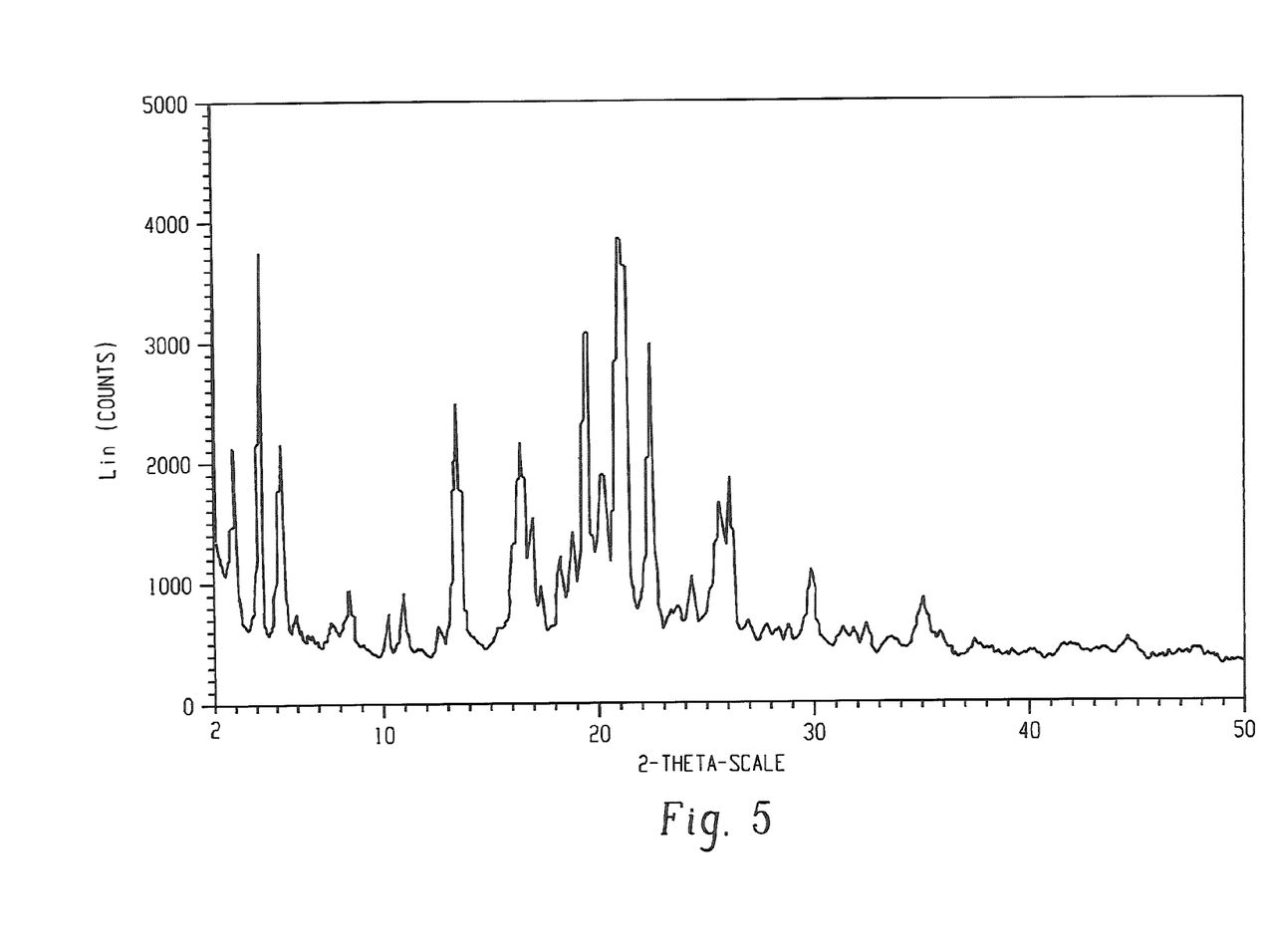
FIG. 5 is X-ray powder diffraction spectrum of crystalline raltegravir lithium.

The powdered x-ray diffractogram (PXRD) of crystalline raltegravir lithium is shown in FIG. 5.

Figure 6:
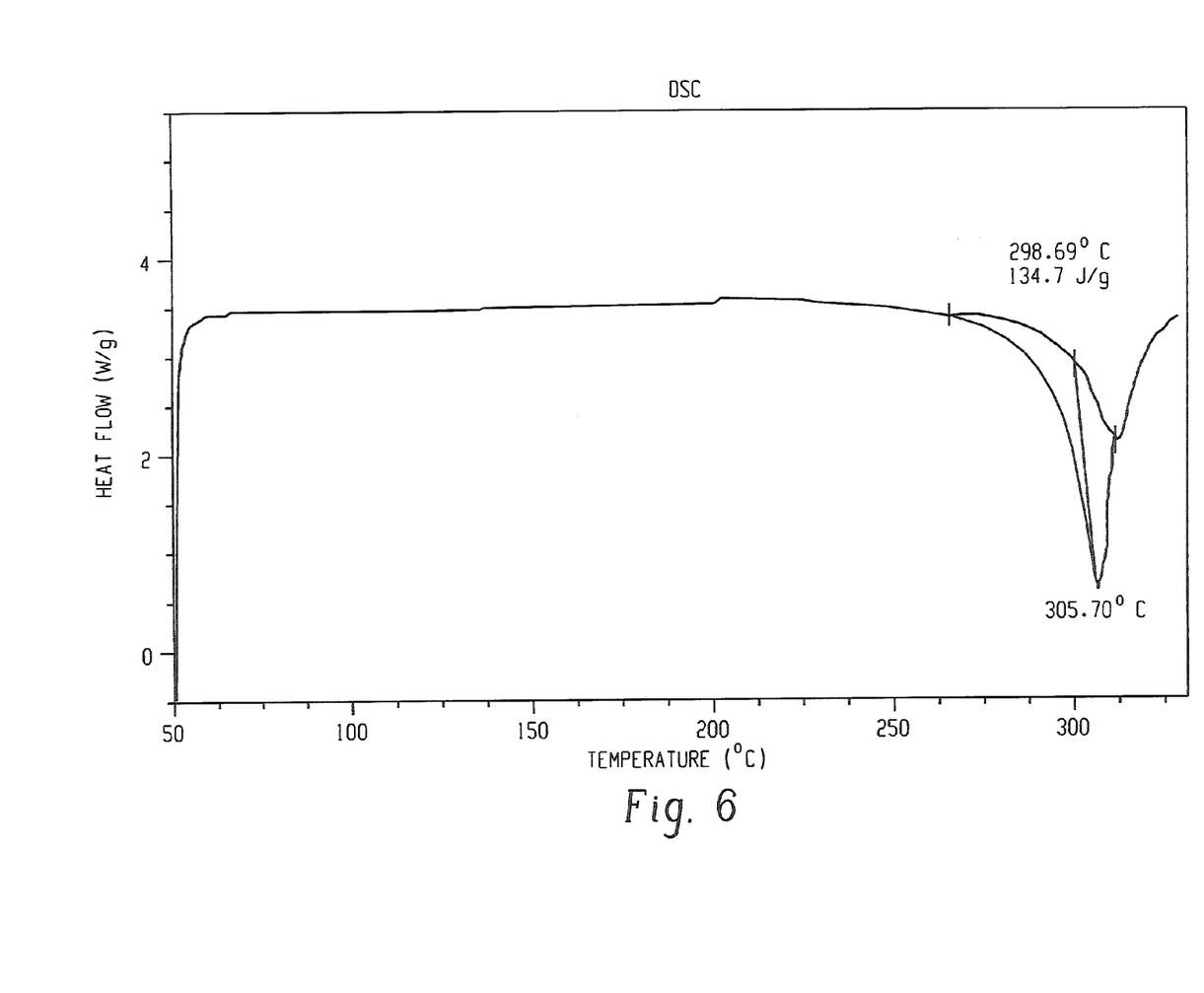
FIG. 6 is Differential scanning calorimetry (DSC) thermogram of crystalline raltegravir lithium.

Crystalline raltegravir lithium of present invention is further characterized by a differential scanning calorimetry (DSC) thermogram as shown in FIG. 6.

According to another aspect of the present invention, there is provided a process for the preparation of raltegravir lithium, which comprises:
a) reacting raltegravir with lithium hydroxide in a suitable solvent;
b) heating the contents to an elevated temperature;
c) removing the solvent from the solution obtained in step (b) to obtain a residual mass;
d) slurrying the residual mass obtained in step (c) with alcoholic solvent; and
e) isolating raltegravir lithium.

The suitable solvent used in step (a) may preferably be a solvent or mixture of solvents selected from the group consisting of water; an alcoholic solvents such as methanol, ethanol and isopropyl alcohol; an ester solvents such as ethyl acetate, methyl acetate, isopropyl acetate, tert-butyl methyl acetate and ethyl formate; a nitrile solvents such as acetonitrile, propionitrile, butyronitrile and benzonitrile; dimethylformamide; dimethylsulfoxide; an aromatic hydrocarbon solvents such as benzene, toluene and xylene; a halogenated hydrocarbon solvents such as methylene chloride, chloroform, carbontetrachloride and ethylene dichloride; a ketonic solvents such as acetone, methyl ethyl ketone, methyl isobutyl ketone and diethyl ketone; an ether solvents such as tetrahydrofuran, 1,4-dioxane, tert-butyl methyl ether and diethyl ether. More preferable solvent is water, alcoholic solvents and nitrile solvents, and still more preferable solvent is water, methanol, ethanol and acetonitrile.

The term "elevated temperature" refers to temperature at above 25° C. Preferably the contents are heating in step (b) at about 60 to 70° C.

Removal of the solvent may be carried out in step (c) at atmospheric pressure or at reduced pressure. Removal of the solvent may preferably be carried out until the solvent is almost completely distilled off.

The aliphatic hydrocarbon solvent used in step (d) may preferably be a solvent or a mixture of solvents selected from cyclohexane, hexane and n-heptane. More preferable aliphatic hydrocarbon solvent is n-heptane.

Isolation of raltegravir lithium in step (e) may preferably be performed by conventional techniques such as centrifugation and filtration.

According to another aspect of the present invention, there is provided a pharmaceutical composition that comprises raltegravir lithium and pharmaceutically acceptable carriers, diluents or excipients and optionally other therapeutic ingredients. The salt may preferable be conveniently formulated into tablets, capsules, suspensions, dispersions, injectables and other pharmaceutical forms.

According to another aspect of the present invention, there is provided crystalline sodium salt of raltegravir.

According to another aspect of the present invention, there is provided a process for the preparation of crystalline raltegravir sodium, which comprises:
 a) suspending raltegravir in an alcoholic solvent;
 b) adding sodium hydroxide to the suspension obtained in step (a);
 c) slurrying the reaction mass obtained in step (b) at about 25 to 30° C.; and
 d) isolating crystalline raltegravir sodium.

The alcoholic solvent used in step (a) may preferably be a solvent or mixture of solvents selected from methanol, ethanol and isopropyl alcohol. More preferable alcoholic solvent is ethanol.

Isolation of crystalline raltegravir sodium in step (d) may preferably be performed by conventional techniques such as centrifugation and filtration.

According to another aspect of the present invention, there is provided a process for the preparation of crystalline form 1 of raltegravir sodium, which comprises:
 a) suspending raltegravir in an alcoholic solvent;
 b) adding sodium hydroxide to the suspension obtained in step (a);
 c) slurrying the reaction mass obtained in step (b) for 10 to 12 hours at about 25 to 30° C.; and
 d) isolating raltegravir sodium crystalline form 1.

Figure 7:
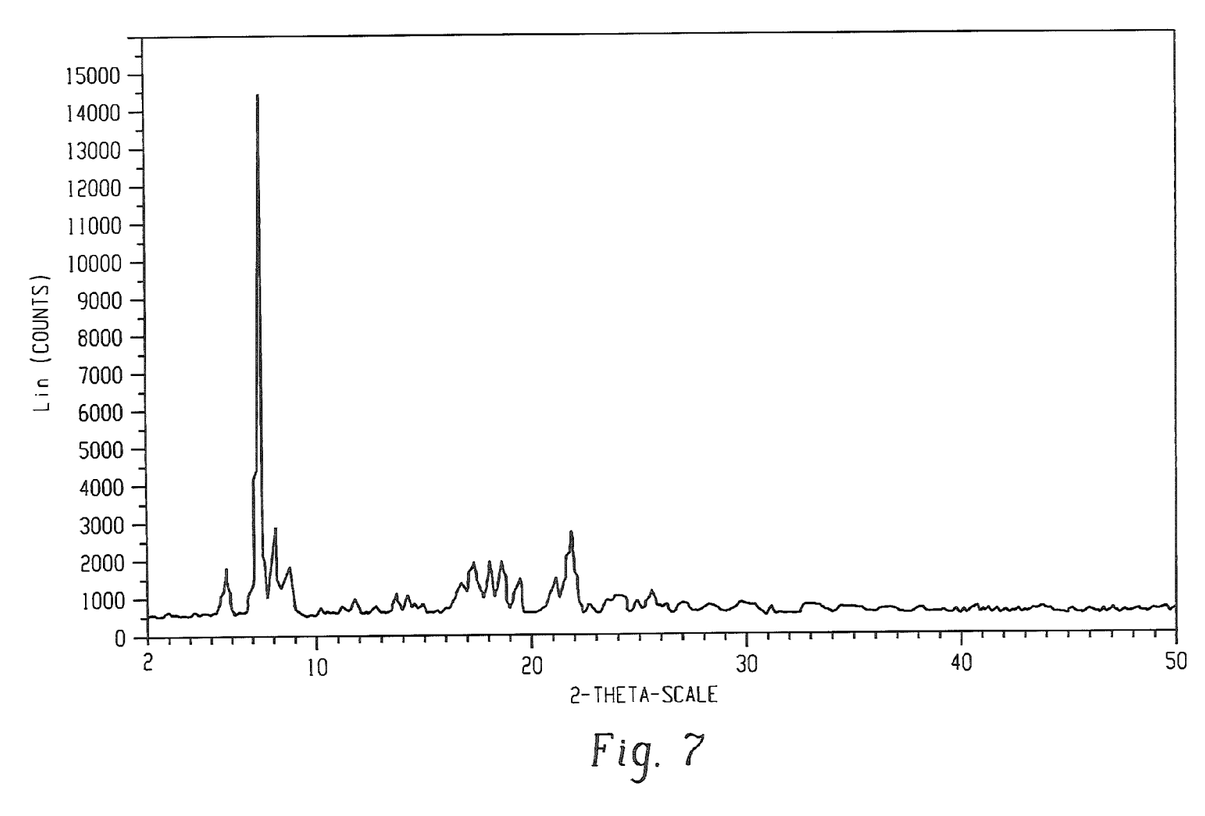
FIG. 7 is X-ray powder diffraction spectrum of raltegravir sodium crystalline form 1.

Raltegravir sodium crystalline form 1, which is characterized by peaks in the powder x-ray diffraction spectrum having 2θ angle positions at about 7.2, 8.0, 18.0, 18.5 and 21.8±0.2 degrees. The powdered x-ray diffractogram (PXRD) of raltegravir sodium crystalline form 1 is shown in FIG. 7.

The alcoholic solvent used in step (a) may preferably be a solvent or mixture of solvents selected from methanol, ethanol and isopropyl alcohol. More preferable alcoholic solvent is ethanol.

Isolation of raltegravir sodium crystalline form 1 in step (d) may preferably be performed by conventional techniques such as centrifugation and filtration.

According to another aspect of the present invention, there is provided a process for the preparation of crystalline form 2 of raltegravir sodium, which comprises:
 a) suspending raltegravir in an alcoholic solvent;
 b) adding sodium hydroxide to the suspension obtained in step (a);
 c) slurrying the reaction mass obtained in step (b) for 30 to 35 hours at about 25 to 30° C.; and
 d) isolating raltegravir sodium crystalline form 2.

Figure 8:
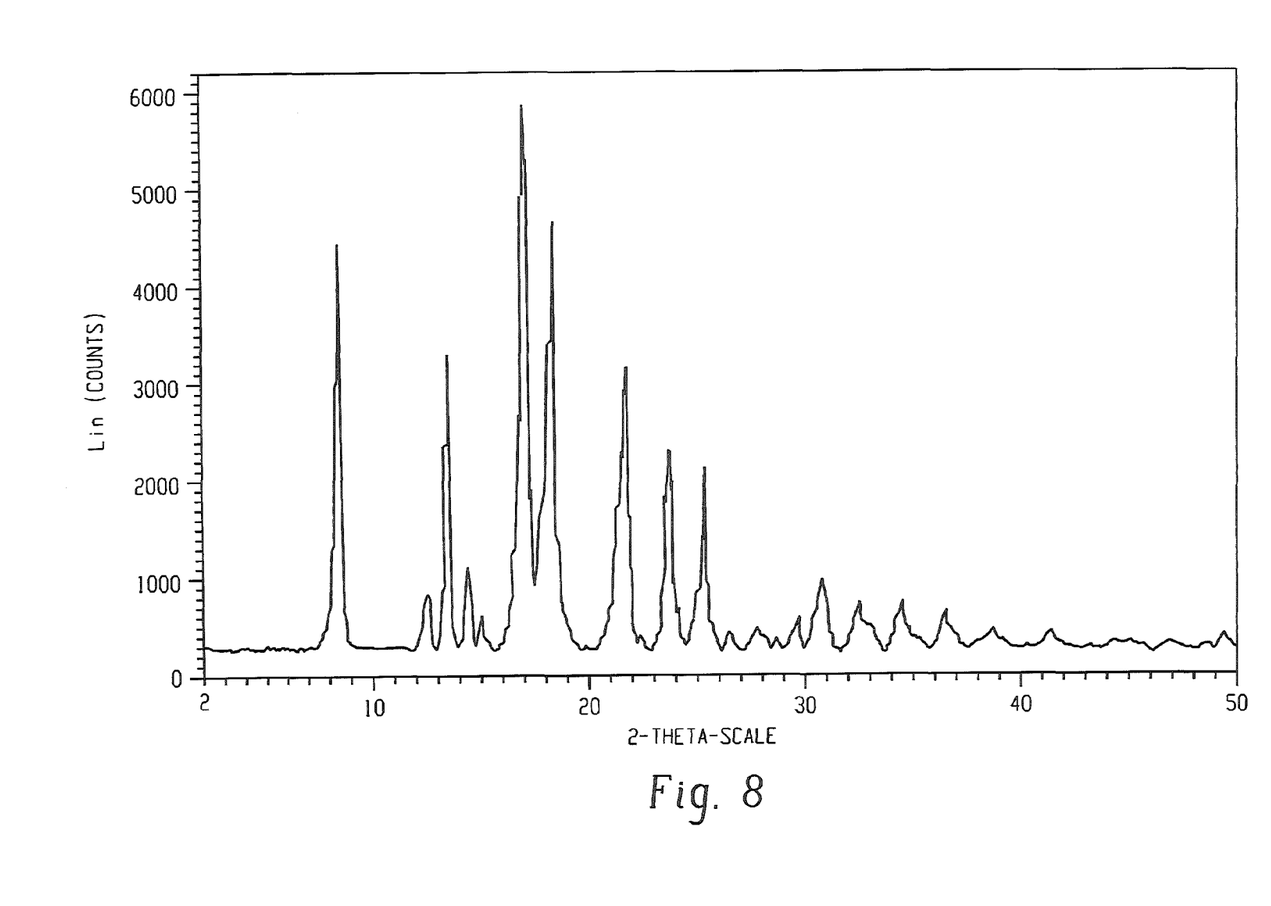
FIG. 8 is X-ray powder diffraction spectrum of raltegravir sodium crystalline form 2.

Raltegravir sodium crystalline form 2, which is characterized by peaks in the powder x-ray diffraction spectrum having 2θ angle positions at about 8.4, 17.0, 17.9, 18.3, 21.3, 21.8 and 23.7±0.2 degrees. The powdered x-ray diffractogram (PXRD) of raltegravir sodium crystalline form 2 is shown in FIG. 8.

The alcoholic solvent used in step (a) may preferably be a solvent or mixture of solvents selected from methanol, ethanol and isopropyl alcohol. More preferable alcoholic solvent is ethanol.

Isolation of raltegravir sodium crystalline form 2 in step (d) may preferably be performed by conventional techniques such as centrifugation and filtration.

According to another aspect of the present invention, there is provided a pharmaceutical composition that comprises crystalline raltegravir sodium and pharmaceutically acceptable carriers, diluents or excipients and optionally other therapeutic ingredients. The salt may preferable be conveniently formulated into tablets, capsules, suspensions, dispersions, injectables and other pharmaceutical forms.

According to another aspect of the present invention, there is provided a process for the preparation of amorphous raltegravir sodium, which comprises:
 a) reacting raltegravir with sodium hydroxide in a suitable solvent;
 b) heating the contents to an elevated temperature;
 c) removing the solvent from the solution obtained in step (b) to obtain a residual mass;
 d) slurrying the residual mass obtained in step (c) with alcoholic solvent; and
 e) isolating amorphous raltegravir sodium.

Figure 9:
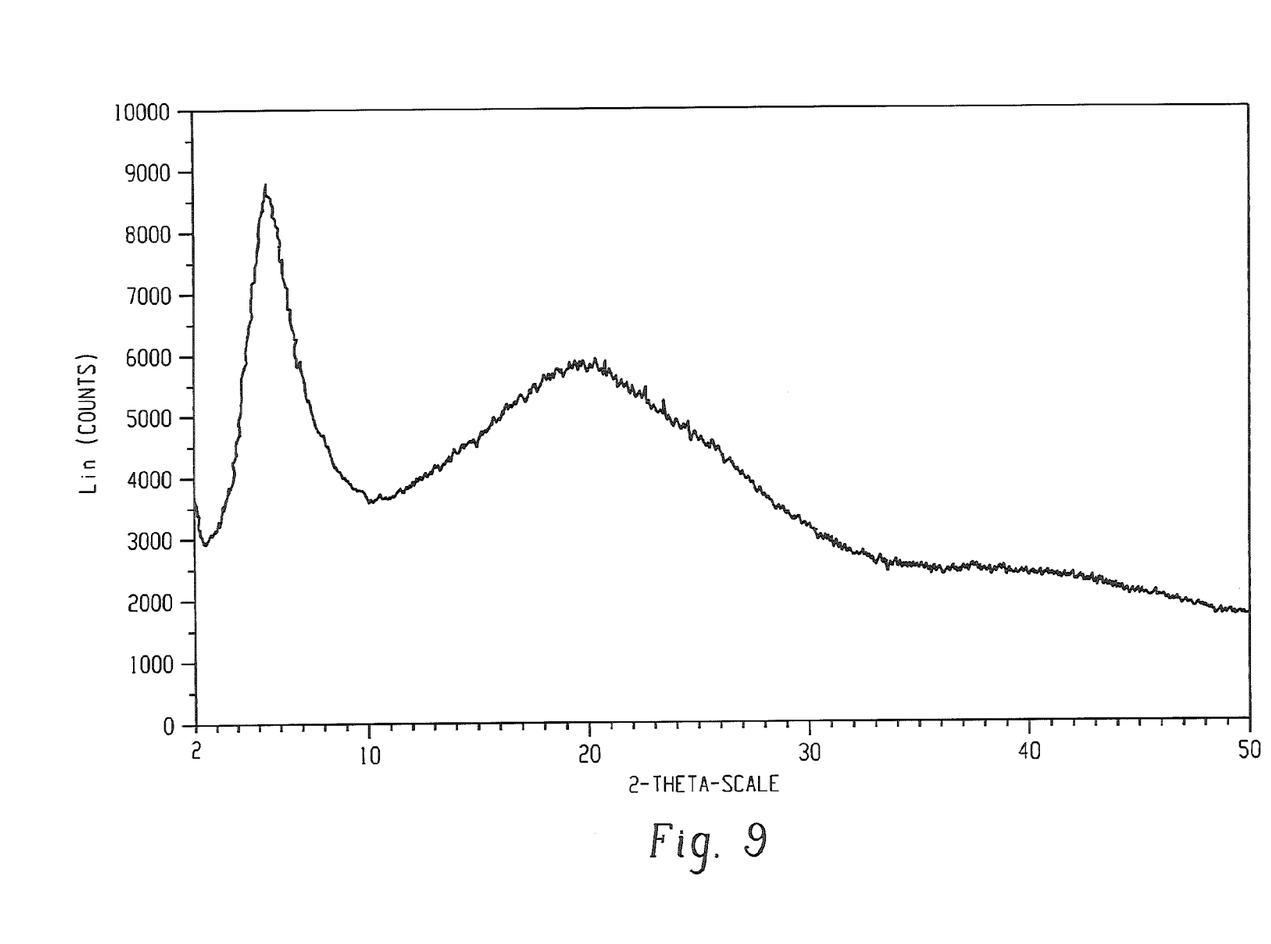
FIG. 9 is X-ray powder diffraction spectrum of amorphous raltegravir sodium.

The powdered x-ray diffractogram (PXRD) of amorphous raltegravir sodium is shown in FIG. 9.

Figure 10:
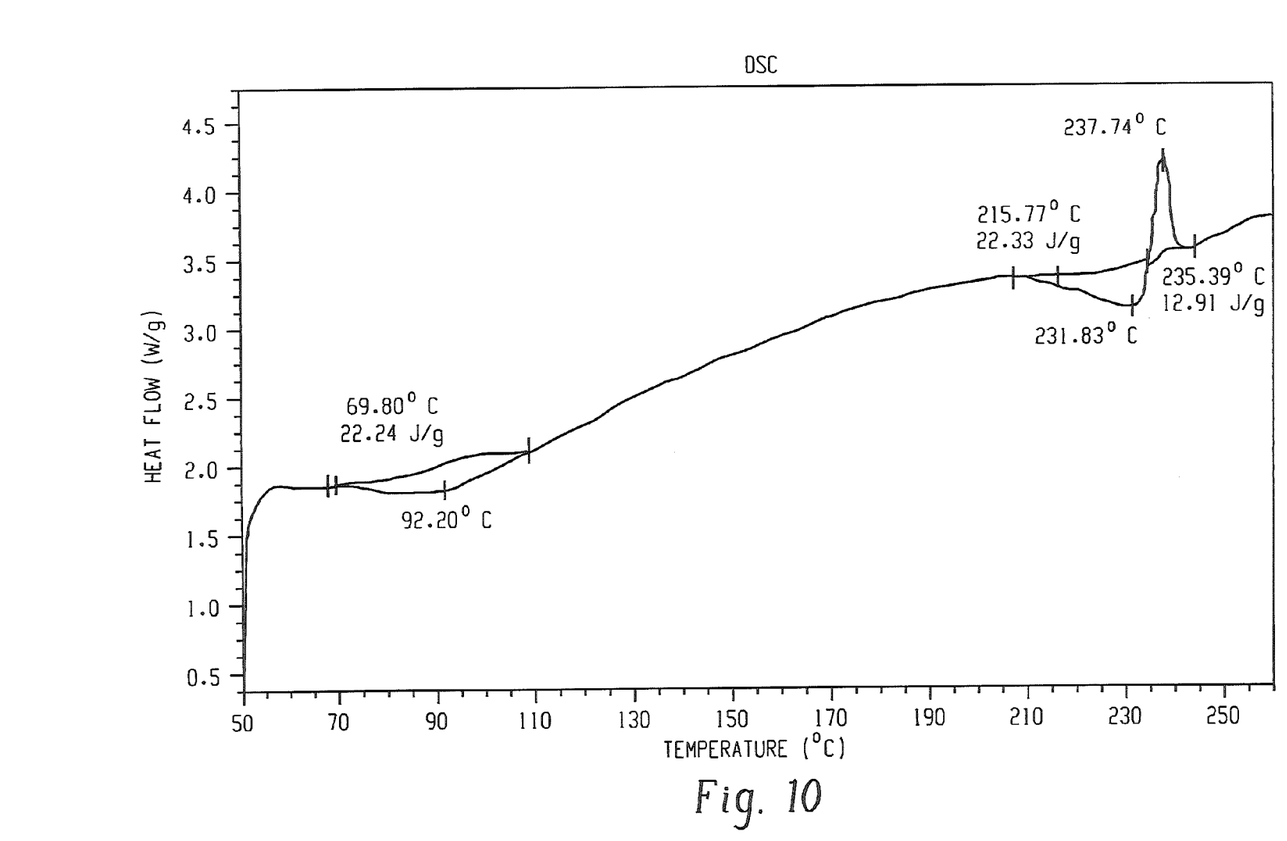
FIG. 10 is Differential scanning calorimetry (DSC) thermogram of amorphous raltegravir sodium.

Amorphous raltegravir sodium of present invention is further characterized by a differential scanning calorimetry (DSC) thermogram as shown in FIG. 10.

The suitable solvent used in step (a) may preferably be a solvent or mixture of solvents selected from the group consisting of water; an alcoholic solvents such as methanol, ethanol and isopropyl alcohol; an ester solvents such as ethyl acetate, methyl acetate, isopropyl acetate, tert-butyl methyl acetate and ethyl formate; a nitrile solvents such as acetonitrile, propionitrile, butyronitrile and benzonitrile; dimethylformamide; dimethylsulfoxide; an aromatic hydrocarbon solvents such as benzene, toluene and xylene; a halogenated hydrocarbon solvents such as methylene chloride, chloroform, carbontetrachloride and ethylene dichloride; a ketonic solvents such as acetone, methyl ethyl ketone, methyl isobutyl ketone and diethyl ketone; an ether solvents such as tetrahydrofuran, 1,4-dioxane, tert-butyl methyl ether and diethyl ether. More preferable solvent is water, alcoholic solvents and nitrile solvents, and still more preferable solvent is water, methanol, ethanol and acetonitrile.

The term "elevated temperature" refers to temperature at above 25° C. Preferably the contents are heating in step (b) at about 60 to 70° C.

Removal of the solvent may be carried out in step (c) at atmospheric pressure or at reduced pressure. Removal of the solvent may preferably be carried out until the solvent is almost completely distilled off.

The aliphatic hydrocarbon solvent used in step (d) may preferably be a solvent or a mixture of solvents selected from cyclohexane, hexane and n-heptane. More preferable aliphatic hydrocarbon solvent is n-heptane.

Isolation of amorphous raltegravir sodium in step (e) may preferably be performed by conventional techniques such as centrifugation and filtration.

According to another aspect of the present invention, there is provided a process for the preparation of raltegravir potassium crystalline form H1, which comprises:
   a) suspending raltegravir in an alcoholic solvent;
   b) adding potassium hydroxide to the suspension obtained in step (a);
   c) slurrying the reaction mass obtained in step (b) at about 25 to 30° C.; and
   d) isolating raltegravir potassium crystalline form H1.

The alcoholic solvent used in step (a) may preferably be a solvent or mixture of solvents selected from methanol, ethanol and isopropyl alcohol. More preferable alcoholic solvent is ethanol.

Isolation of raltegravir potassium crystalline form H1 in step (d) may preferably be performed by conventional techniques such as centrifugation and filtration.

The invention will now be further described by the following examples, which are illustrative rather than limiting.

EXAMPLES

Example 1

Preparation of Raltegravir Barium

Raltegravir (100 gm), ethanol (600 ml), acetonitrile (400 ml) and barium hydroxide (42 gm) were added at 25 to 30° C. The contents were heated to 60 to 65° C. to obtain a solution. The solution was cooled to 25 to 30° C. and stirred for 18 hours at 25 to 30° C. The solid obtained was collected by filtration and dried to obtain 108 gm of raltegravir barium.

Example 2

Preparation of Raltegravir Barium

Raltegravir (10 gm), methanol (60 ml), acetonitrile (40 ml) and barium hydroxide (4.2 gm) were added at 25 to 30° C. The contents were heated to 60 to 65° C. to obtain a solution. The solution was cooled to 25 to 30° C. and stirred for 20 hours at 25 to 30° C. The solid obtained was collected by filtration and dried to obtain 10 gm of raltegravir barium.

Example 3

Preparation of Raltegravir Barium

Raltegravir (100 gm) was suspended in ethanol (600 ml) and then added barium hydroxide (42 gm) at 25 to 30° C. The contents were heated to 60 to 65° C. to obtain a solution. The solution was cooled to 25 to 30° C. and stirred for 18 hours at 25 to 30° C. The solid obtained was collected by filtration and dried to obtain 105 gm of raltegravir barium.

Example 4

Preparation of Raltegravir Barium

Raltegravir (100 gm) was suspended in acetonitrile (400 ml) and then added barium hydroxide (42 gm) at 25 to 30° C. The contents were heated to 60 to 65° C. to obtain a solution. The solution was cooled to 25 to 30° C. and stirred for 18 hours at 25 to 30° C. The solid obtained was collected by filtration and dried to obtain 105 gm of raltegravir barium.

Example 5

Preparation of Raltegravir Calcium

Raltegravir (10 gm), ethanol (60 ml), acetonitrile (40 ml), water (2 ml) and calcium acetate (4 gm) were added at 25 to 30° C. The contents were heated to 65 to 70° C. and distilled off solvent completely under vacuum at 45° C. to obtain residue. To the residue was added n-heptane (50 ml) and again distilled to obtain residue. n-Heptane (100 ml) was added to the residue and stirred for 6 hours at room temperature. The solid obtained was collected by filtration and dried to obtain 10.2 gm of raltegravir calcium.

Example 6

Preparation of Raltegravir Calcium

Raltegravir (10 gm), methanol (60 ml), acetonitrile (40 ml), water (2 ml) and calcium acetate (4 gm) were added at 25 to 30° C. The contents were heated to 65 to 70° C. and distilled off solvent completely under vacuum at 45° C. to obtain residue. To the residue was added n-heptane (50 ml) and again distilled to obtain residue. n-Heptane (100 ml) was added to the residue and stirred for 6 hours at room temperature. The solid obtained was collected by filtration and dried to obtain 9.8 gm of raltegravir calcium.

Example 7

Preparation of Raltegravir Calcium

Raltegravir (10 gm), ethanol (60 ml), acetonitrile (40 ml), water (2 ml) and calcium acetate (4 gm) were added at 25 to 30° C. The contents were heated to 65 to 70° C. and distilled off solvent completely under vacuum at 45° C. to obtain residue. To the residue was added cyclohexane (50 ml) and again distilled to obtain residue. Cyclohexane (100 ml) was added to the residue and stirred for 5 hours at room temperature. The solid obtained was collected by filtration and dried to obtain 10 gm of raltegravir calcium.

Example 8

Preparation of Raltegravir Calcium

Raltegravir (10 gm) was suspended in ethanol (60 ml) and then added a solution of calcium acetate (4 gm) in water (2 ml) at 25 to 30° C. The contents were heated to 65 to 70° C. and distilled off solvent completely under vacuum at 45° C. to obtain residue. To the residue was added n-heptane (50 ml) and again distilled to obtain residue. n-Heptane (100 ml) was added to the residue and stirred for 6 hours at room temperature. The solid obtained was collected by filtration and dried to obtain 9.9 gm of raltegravir calcium.

Example 9

Preparation of Raltegravir Calcium

Raltegravir (10 gm) was suspended in acetonitrile (40 ml) and then added a solution of calcium acetate (4 gm) in water (2 ml) at 25 to 30° C. The contents were heated to 65 to 70° C. and distilled off solvent completely under vacuum at 45° C. to obtain residue. To the residue was added n-heptane (50 ml) and again distilled to obtain residue. n-Heptane (100 ml) was added to the residue and stirred for 6 hours at room temperature. The solid obtained was collected by filtration and dried to obtain 9.8 gm of raltegravir calcium.

Example 10

Preparation of Raltegravir Lithium

Raltegravir (10 gm), ethanol (60 ml), acetonitrile (40 ml), water (2 ml) and lithium hydroxide (0.7 gm) were added at 25 to 30° C. The contents were heated to 65 to 70° C. and distilled off solvent completely under vacuum at 45° C. to obtain residue. To the residue was added ethanol (50 ml) and stirred for 6 hours at room temperature. The solid obtained was collected by filtration and dried to obtain 10.1 gm of raltegravir lithium.

Example 11

Preparation of Raltegravir Lithium

Raltegravir (10 gm), methanol (60 ml), acetonitrile (40 ml), water (2 ml) and lithium hydroxide (0.7 gm) were added at 25 to 30° C. The contents were heated to 65 to 70° C. and distilled off solvent completely under vacuum at 45° C. to obtain residue. To the residue was added ethanol (50 ml) and stirred for 6 hours at room temperature. The solid obtained was collected by filtration and dried to obtain 9.8 gm of raltegravir lithium.

Example 12

Preparation of Raltegravir Lithium

Raltegravir (10 gm) was suspended in ethanol (60 ml) and then added a solution of lithium hydroxide (0.7 gm) in water (2 ml) at 25 to 30° C. The contents were heated to 65 to 70° C. and distilled off solvent completely under vacuum at 45° C. to obtain residue. To the residue was added ethanol (50 ml) and stirred for 5 hours at room temperature. The solid obtained was collected by filtration and dried to obtain 10 gm of raltegravir lithium.

Example 13

Preparation of Raltegravir Lithium

Raltegravir (10 gm) was suspended in acetonitrile (40 ml) and then added a solution of lithium hydroxide (0.7 gm) in water (2 ml) at 25 to 30° C. The contents were heated to 65 to 70° C. and distilled off solvent completely under vacuum at 45° C. to obtain residue. To the residue was added ethanol (50 ml) and stirred for 5 hours at room temperature. The solid obtained was collected by filtration and dried to obtain 9.9 gm of raltegravir lithium.

Example 14

Preparation of Raltegravir Sodium Crystalline Form 1

Raltegravir (50 gm) was suspended in ethanol (500 ml) and then added a solution of sodium hydroxide (5 gm) in water (10 ml) at 25 to 30° C. The reaction mass was stirred for 11 hours at 25 to 30° C. and filtered. The solid obtained was dried under vacuum at 60° C. for 7 hours to obtain 52 gm of raltegravir sodium crystalline form 1.

Example 15

Preparation of Raltegravir Sodium Crystalline Form 1

Raltegravir (50 gm) was suspended in ethanol (500 ml) and then added sodium hydroxide (5 gm) at 25 to 30° C. The reaction mass was stirred for 12 hours at 25 to 30° C. and filtered. The solid obtained was dried under vacuum at 60° C. for 7 hours to obtain 50 gm of raltegravir sodium crystalline form 1.

Example 16

Preparation of Raltegravir Sodium Crystalline Form 2

Raltegravir (100 gm) was suspended in ethanol (1000 ml) and then added a solution of sodium hydroxide (10 gm) in water (20 ml) at 25 to 30° C. The reaction mass was stirred for 32 hours at 25 to 30° C. and filtered. The solid obtained was dried under vacuum at 60° C. for 8 hours to obtain 105 gm of raltegravir sodium crystalline form 2.

Example 17

Preparation of Raltegravir Sodium Crystalline Form 2

Raltegravir (100 gm) was suspended in ethanol (1000 ml) and then added sodium hydroxide (10 gm) at 25 to 30° C. The reaction mass was stirred for 34 hours at 25 to 30° C. and filtered. The solid obtained was dried under vacuum at 60° C. for 8 hours to obtain 102 gm of raltegravir sodium crystalline form 2.

Example 18

Preparation of Amorphous Raltegravir Sodium

Raltegravir (10 gm), ethanol (60 ml), acetonitrile (40 ml), water (2 ml) and sodium hydroxide (1 gm) were added at 25 to 30° C. The contents were heated to 65 to 70° C. and distilled off solvent completely under vacuum at 45° C. to obtain residue. To the residue was added n-heptane (50 ml) and again distilled to obtain residue. n-Heptane (100 ml) was added to the residue and stirred for 6 hours at room temperature. The solid obtained was collected by filtration and dried to obtain 10 gm of amorphous raltegravir sodium.

Example 19

Preparation of Amorphous Raltegravir Sodium

Raltegravir (50 gm), ethanol (300 ml), acetonitrile (200 ml), water (10 ml) and sodium hydroxide (5 gm) were added at 25 to 30° C. The contents were heated to 65 to 70° C. and distilled off solvent completely under vacuum at 45° C. to obtain residue. To the residue was added cyclohexane (250 ml) and again distilled to obtain residue. Cyclohexane (500 ml) was added to the residue and stirred for 5 hours at room temperature. The solid obtained was collected by filtration and dried to obtain 48 gm of amorphous raltegravir sodium.

Example 20

Preparation of Amorphous Raltegravir Sodium

Raltegravir (10 gm), methanol (60 ml), acetonitrile (40 ml), water (2 ml) and sodium hydroxide (1 gm) were added at 25 to 30° C. The contents were heated to 65 to 70° C. and distilled off solvent completely under vacuum at 45° C. to obtain residue. To the residue was added n-heptane (50 ml) and again distilled to obtain residue. n-Heptane (100 ml) was added to the residue and stirred for 6 hours at room temperature. The solid obtained was collected by filtration and dried to obtain 9.8 gm of amorphous raltegravir sodium.

Example 21

Preparation of Raltegravir Potassium Crystalline form H1

Raltegravir (50 gm) was suspended in ethanol (500 ml) and then added a solution of potassium hydroxide (8 gm) in water (10 ml) at 25 to 30° C. The reaction mass was stirred for 16 hours at 25 to 30° C. and filtered. The solid obtained was dried under vacuum at 60° C. for 9 hours to obtain 52 gm of raltegravir potassium crystalline form H1.

Example 22

Preparation of Raltegravir Potassium Crystalline Form H1

Raltegravir (50 gm) was suspended in ethanol (500 ml) and then added potassium hydroxide (8 gm) at 25 to 30° C. The reaction mass was stirred for 18 hours at 25 to 30° C. and filtered. The solid obtained was dried under vacuum at 60° C. for 9 hours to obtain 50 gm of raltegravir potassium crystalline form 1-11.

Example 23

Preparation of Raltegravir Potassium Crystalline Form H1

Raltegravir (50 gm) was suspended in isopropyl alcohol (500 ml) and then added a solution of potassium hydroxide (8 gm) in water (10 ml) at 25 to 30° C. The reaction mass was stirred for 17 hours at 25 to 30° C. and filtered. The solid obtained was dried under vacuum at 60° C. for 9 hours to obtain 48 gm of raltegravir potassium crystalline form H1.

Figure 11:
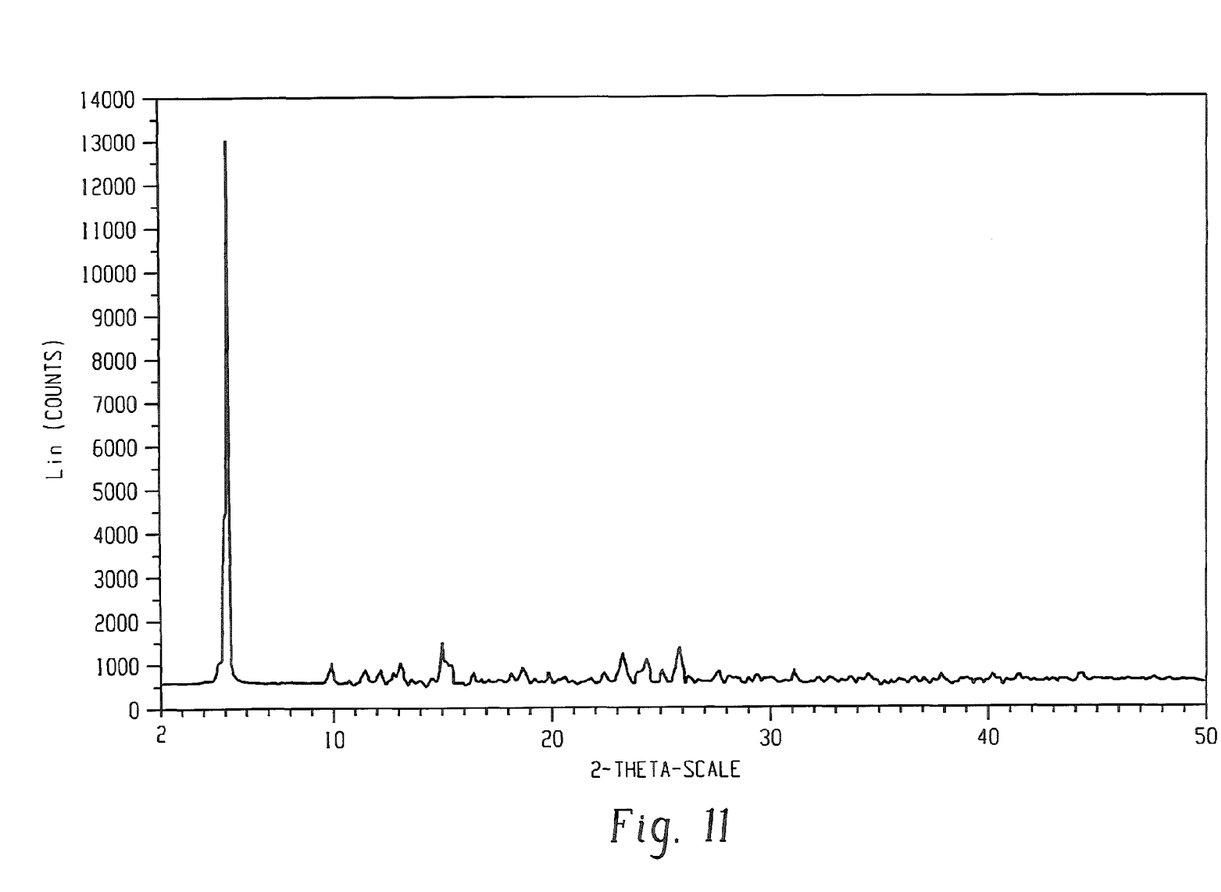
FIG. 11 is X-ray powder diffraction spectrum of raltegravir potassium crystalline form H1.

We claim:

1. A process for the preparation of raltegravir potassium crystalline form H1, comprising:
   a. suspending raltegravir in an non-aqueous alcoholic solvent to provide a suspension;
   b. adding potassium hydroxide to the suspension obtained in step (a) to provide a reaction mass;
   c. stirring the reaction mass obtained in step (b) at about 25 to 30° C. to provide a slurry, wherein stirring is for a time sufficient to produce raltegravir potassium crystalline form H1 and wherein stirring is for 16 hours or more; and
   d. isolating raltegravir potassium crystalline form H1 from the slurry, wherein raltegravir potassium crystalline form H1 is in accordance with FIG. 11.

2. The process according to claim 1, wherein the non-aqueous alcohol solvent used in step (a) is a solvent or mixture of solvents selected from methanol, ethanol and isopropyl alcohol.

3. The process according to claim 2, wherein the non-aqueous alcoholic solvent is ethanol.

* * * * *